(12) United States Patent
Ferek-Petric

(10) Patent No.: US 6,514,195 B1
(45) Date of Patent: Feb. 4, 2003

(54) ISCHEMIC HEART DISEASE DETECTION

(75) Inventor: Bozidar Ferek-Petric, Zagreb (HR)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/558,870

(22) Filed: Apr. 28, 2000

(51) Int. Cl.$^7$ .............................................. A61N 1/362
(52) U.S. Cl. ............................................. 600/17; 607/6
(58) Field of Search .................. 600/17, 374, 438, 600/454, 467, 468, 504, 505, 509, 513, 516, 517, 519; 607/4, 5, 9, 11, 17, 62, 66, 119, 120, 122

(56) References Cited

U.S. PATENT DOCUMENTS

| | | |
|---|---|---|
| 4,316,472 A | 2/1982 | Mirowski et al. |
| 4,375,817 A | 3/1983 | Engle et al. |
| 4,384,585 A | 5/1983 | Zipes |
| 4,566,063 A | 1/1986 | Zolnowski et al. |
| 4,577,633 A | 3/1986 | Berkovits et al. |
| 4,587,970 A | 5/1986 | Holley et al. |
| 4,719,201 A * | 1/1988 | Foker ........................... 514/23 |
| 4,726,380 A | 2/1988 | Vollmann et al. |
| 4,727,877 A | 3/1988 | Kallok |
| 4,800,883 A | 1/1989 | Winstrom |
| 4,821,723 A | 4/1989 | Baker, Jr. et al. |
| 4,830,006 A | 5/1989 | Haluska et al. |
| 4,880,005 A | 11/1989 | Pless et al. |
| 4,949,719 A | 8/1990 | Pless et al. |
| 4,953,551 A | 9/1990 | Mehra et al. |
| 5,117,824 A | 6/1992 | Keimel et al. |
| 5,131,388 A | 7/1992 | Pless et al. |
| 5,135,004 A * | 8/1992 | Adams et al. .............. 128/696 |
| 5,144,949 A | 9/1992 | Olson |
| 5,163,427 A | 11/1992 | Keimel |
| 5,178,078 A | 1/1993 | Pendergrass |
| 5,188,105 A | 2/1993 | Keimel |
| 5,199,428 A | 4/1993 | Obel et al. |
| 5,207,218 A | 5/1993 | Carpentier et al. |
| 5,269,298 A | 12/1993 | Adams et al. |
| 5,305,745 A | 4/1994 | Zacouto |
| 5,312,453 A | 5/1994 | Shelton et al. |
| 5,316,001 A * | 5/1994 | Ferek-Petric ........... 128/661.08 |
| 5,330,507 A | 7/1994 | Schwartz |
| 5,331,966 A | 7/1994 | Bennett et al. |
| 5,354,316 A | 10/1994 | Keimel |
| 5,545,186 A | 8/1996 | Olson et al. |
| 5,800,465 A | 9/1998 | Thompson et al. |
| 6,206,914 B1 * | 3/2001 | Soykan et al. .............. 623/1.42 |
| 6,243,603 B1 * | 6/2001 | Ideker et al. ................... 607/5 |

FOREIGN PATENT DOCUMENTS

WO      WO92/18198      10/1992

OTHER PUBLICATIONS

"Automatic Tachycardia Recognition" Arzbaecher et al, Pace, May–Jun., 1984, pp. 541–547.

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

* cited by examiner

*Primary Examiner*—Jeffrey R. Jastrzab
*Assistant Examiner*—Frances P. Oropeza
(74) *Attorney, Agent, or Firm*—Thomas F. Woods; Eric R. Waldkoetter; Tom G. Berry

(57) ABSTRACT

An implantable medical device system for detecting cardiac conditions such the long-term ischemic heart disease, an occlusion of a coronary artery by a thrombus or an impending as a myocardial infarction. The implantable medical device (IMD) system includes a sensor that outputs a blood flow rate signal representing a rate of blood flow through a coronary sinus of a patient's heart. An implantable medical device (IMD) includes a microcomputer circuit configured to analyze the blood flow rate signal and detect a cardiac condition as a function of the blood flow rate signal. The system can also includes an implantable lead that senses electrical activity from the patient's heart. The microcomputer circuit monitors an ST segment of the electrical activity signal and detects a cardiac condition as a function of blood flow rate signal in conjunction with the electrical activity signal.

28 Claims, 8 Drawing Sheets

ISCHEMIC HEART DISEASE DETECTION

FIELD OF INVENTION

This invention relates generally to the field of implantable medical devices, and more particularly to implantable heart monitors and therapy delivery devices.

BACKGROUND

A wide variety of implantable heart monitors and therapy delivery devices have been developed including pacemakers, cardioverter/defibrillators, heart pumps, cardiomyostimulators, ischemia treatment devices, and drug delivery devices. Most of these cardiac systems include electrodes for sensing and sense amplifiers for recording and/or deriving sense event signals.

These devices typically utilize the sense event signals to detect problems with a patient's cardiac system and to delivery of the therapy. Prior art disclosures have been made suggesting methods for detecting cardiac conditions including:

TABLE 1

| Country | Patent Number | Inventor/Applicant | Issue Date |
| --- | --- | --- | --- |
| U.S.A. | 5,199,428 | Obel et al | 1993 |
| U.S.A. | 5,305,745 | Zacouto | 1994 |

All patents listed in Table 1 above are hereby incorporated by reference herein in their respective entireties. As those of ordinary skill in the art will appreciate readily upon reading the Summary of the Invention, Detailed Description and Claims set forth below, many of the devices and methods disclosed in the patents of Table 1 may be modified advantageously by using the teachings of the present invention.

SUMMARY OF THE INVENTION

The invention has certain objects and, in general, provides solutions to problems existing in the prior art in detecting the onset of a cardiac condition. One of the most dangerous cardiac conditions is a myocardial infarction in which a section of heart muscle dies due to a loss of blood flow from a coronary artery. Most myocardial infarctions occur in the left ventricle and cause sharp pain in the chest, which can spread to the arms and throat. In addition, the invention provides techniques for detecting other cardiac conditions such as an occlusion of a coronary artery by a thrombus or ischemic heart disease. Unlike other known techniques, cardiac conditions are detected, according to the invention, by monitoring the flow of blood as it exits the coronary system through the coronary sinus. In addition, electrical activity in the heart is sensed for any irregularities, such as an elevated ST segment of the heartbeat.

The features of the invention may be incorporated in a variety of embodiments. For example, in one embodiment a system includes a lead for implantation in the coronary sinus of a patient's heart. The lead includes a sensor for measuring the velocity of blood flowing through the coronary sinus. An implantable medical device (IMD) coupled to the lead monitors a blood flow signal from the sensor as well as electrical activity within the heart. The implantable medical device system includes a microprocessor circuit to analyze the blood flow signal and the electrical activity signal in order to detect cardiac conditions.

According to one feature of the invention, the IMD delivers an alarm to the patient or begins delivering drug therapy, preferably delivery of rapid action thrombolytics, as a function of sensed electrical activity and the blood flow through the coronary sinus. For example, the IMD can include an audible alarm, a muscle stimulating alarm or both. In addition, the IMD can include a drug delivery pump for dispensing therapeutic drugs or a catheter to deliver prophylactic arrhythmia therapy. The system can be constructed to vary the treatment, and notably the dosage, according to the sensed elevation of the ST segment and the blood flow.

Various embodiments of the invention are set forth in the accompanying drawings and the description below. Other features and advantages of the invention will become apparent from the description, the drawings, and the claims.

DETAILED DESCRIPTION

Figure 1:
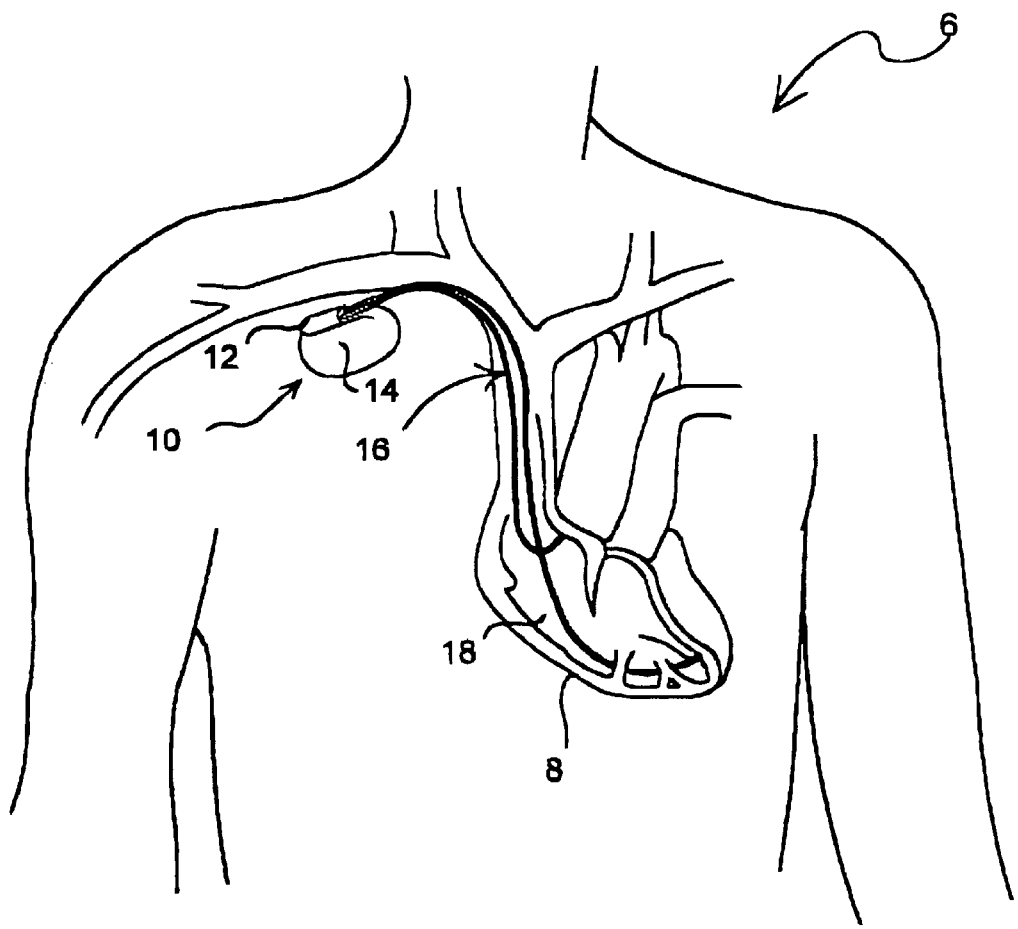
FIG. 1 illustrates an implantable medical device system in accordance with an embodiment of the invention implanted in a human body.

FIG. 1 is a simplified schematic view of one embodiment of implantable medical device ("IMD") 10 of the present invention implanted within a human body 6. IMD 10 comprises hermetically sealed enclosure 14 and connector module 12 for coupling IMD 10 to pacing and sensing leads 16 and 18 that are implanted near heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
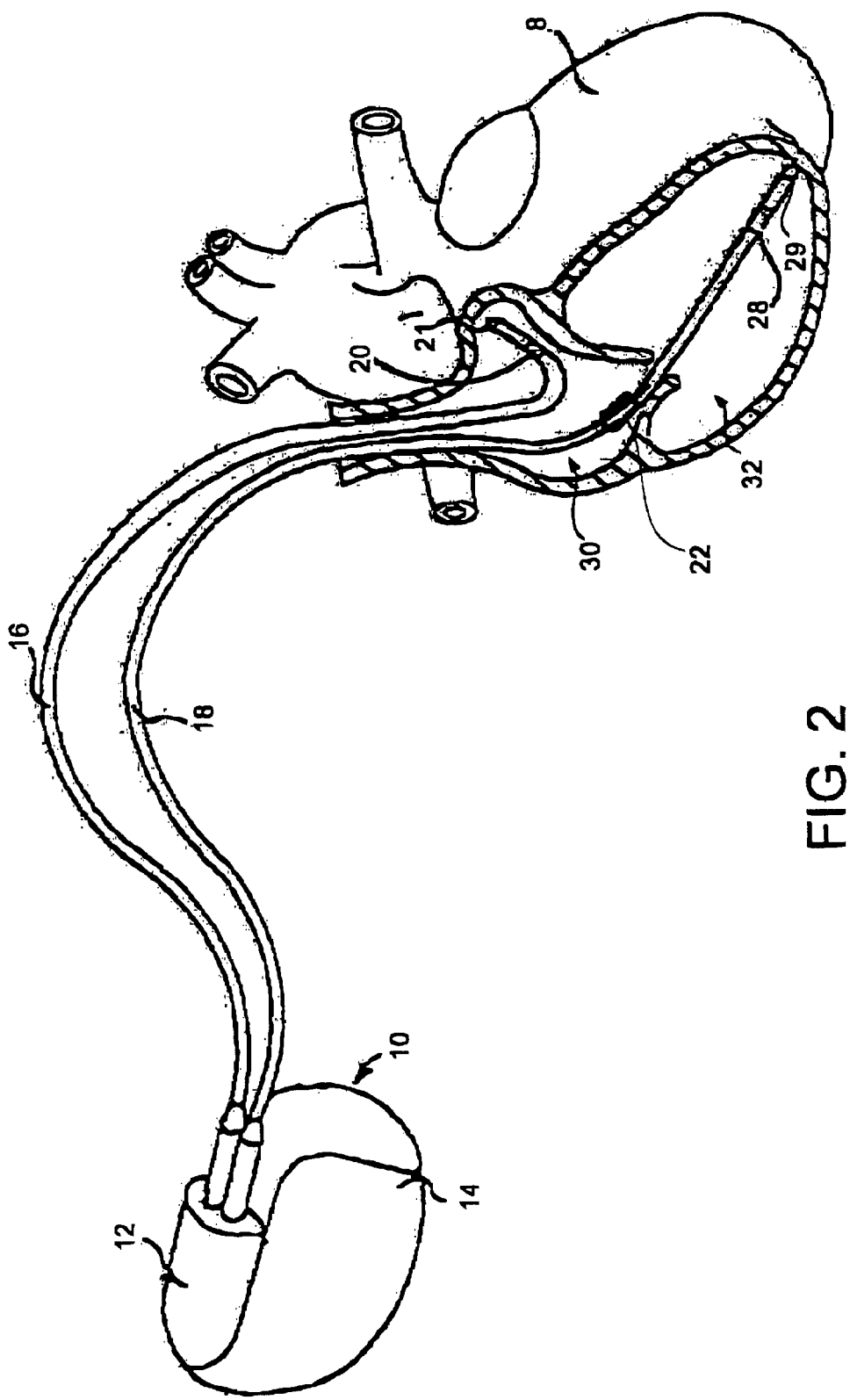
FIG. 2 illustrates one embodiment of an implantable pacemaker device system in accordance with the present invention coupled to a human heart.

FIG. 2 shows connector module 12 and hermetically sealed enclosure 14 of IMD 10 located in and near heart 8. Atrial and ventricular pacing leads 16 and 18 extend from connector module 12 to the right atrium 30 and right ventricle 32, respectively, of heart 8. Atrial electrodes 20 and 21 disposed at the distal end of atrial pacing lead 16 are located in the right atrium 30. Ventricular electrodes 28 and 29 at the distal end of ventricular pacing lead 18 are located in the right ventricle 32. Flow sensor 22 is mounted fixed on the lead 18 for measurement of the blood flow velocity within the heart.

Figure 3:
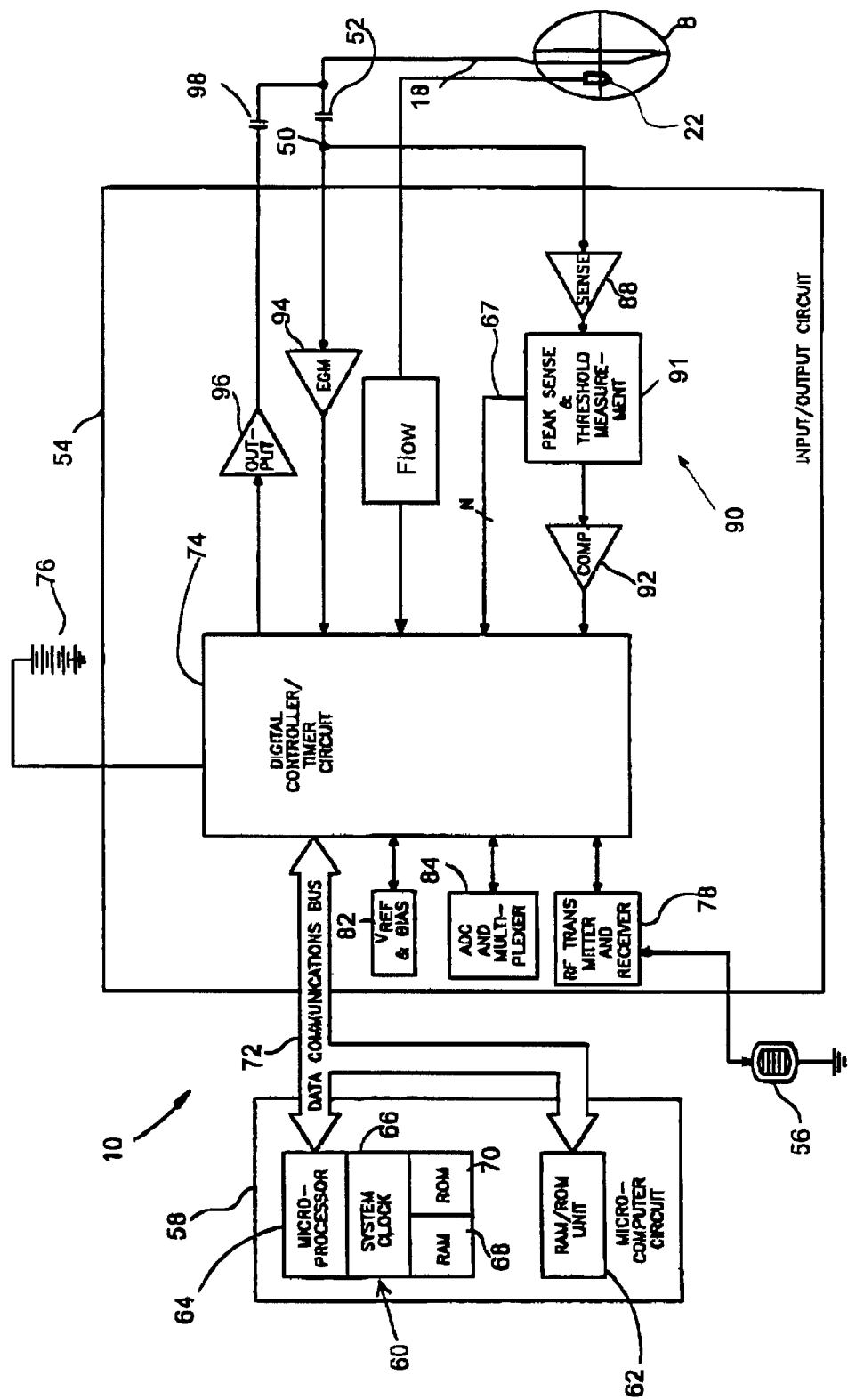
FIG. 3 is a block diagram illustrating the various components of one embodiment of an implantable pacemaker device configured to operate in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including blood flow sensor 22, which is preferably electrochemical or ultrasonic Doppler mounted fixed on the lead x. Blood flow sensor 22 typically (although not necessarily) provides a flow rate signal representing the velocity of blood flowing through the heart. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Blood flow sensor 22 is connected to a flow signal acquisition circuit located inside hermetically sealed enclosure 14 of IMD 10. The output signal provided by flow sensor 22 is coupled to input/output circuit 54. The output signal provided by blood flow sensor 22 is coupled to input/output circuit 54. Input/output circuit 54 contains analog circuits for interfacing to heart 8, blood flow sensor 22, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish an overall escape interval of the IMD 10 as well as various refractory, blanking and other timing windows for controlling the operation of peripheral components disposed within input/output circuit 54.

Digital controller/timer circuit 74 is preferably coupled to sensing circuitry 91, including sense amplifier 88, peak sense and threshold measurement unit 90 and comparator/threshold detector 92. Digital controller/timer circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Measurement of the blood flow parameters, for example, can yield rate-responsive pacing. Some embodiments of the present invention are capable of operating in both non-rate-responsive and rate responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,.821,723 to Baker et al., all hereby incorporated by reference herein, each in its respective entirety.

Figure 4:
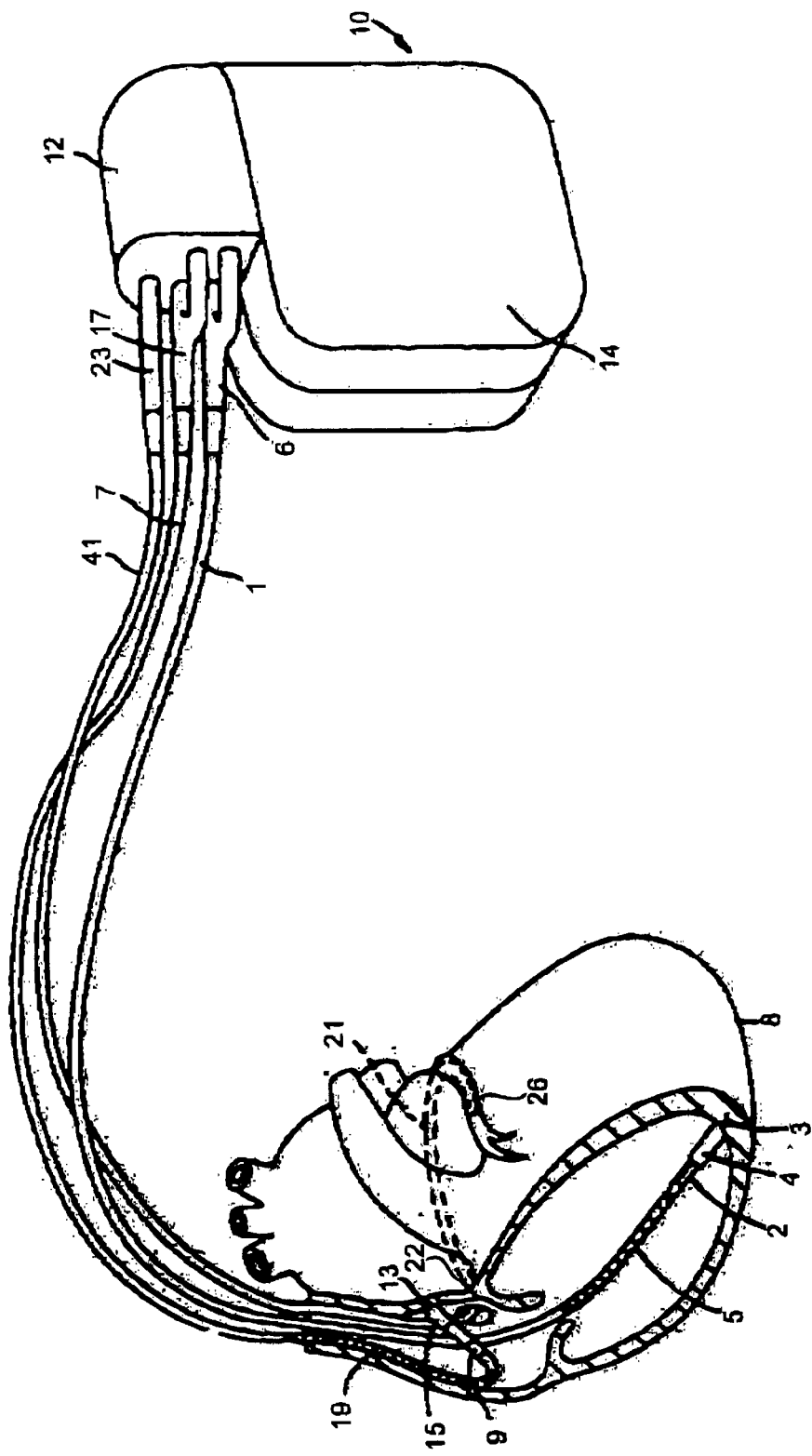
FIG. 4 illustrates one embodiment of an implantable pacemaker cardioverter defibrillator in accordance with the present invention coupled to a human heart.
Figure 5:
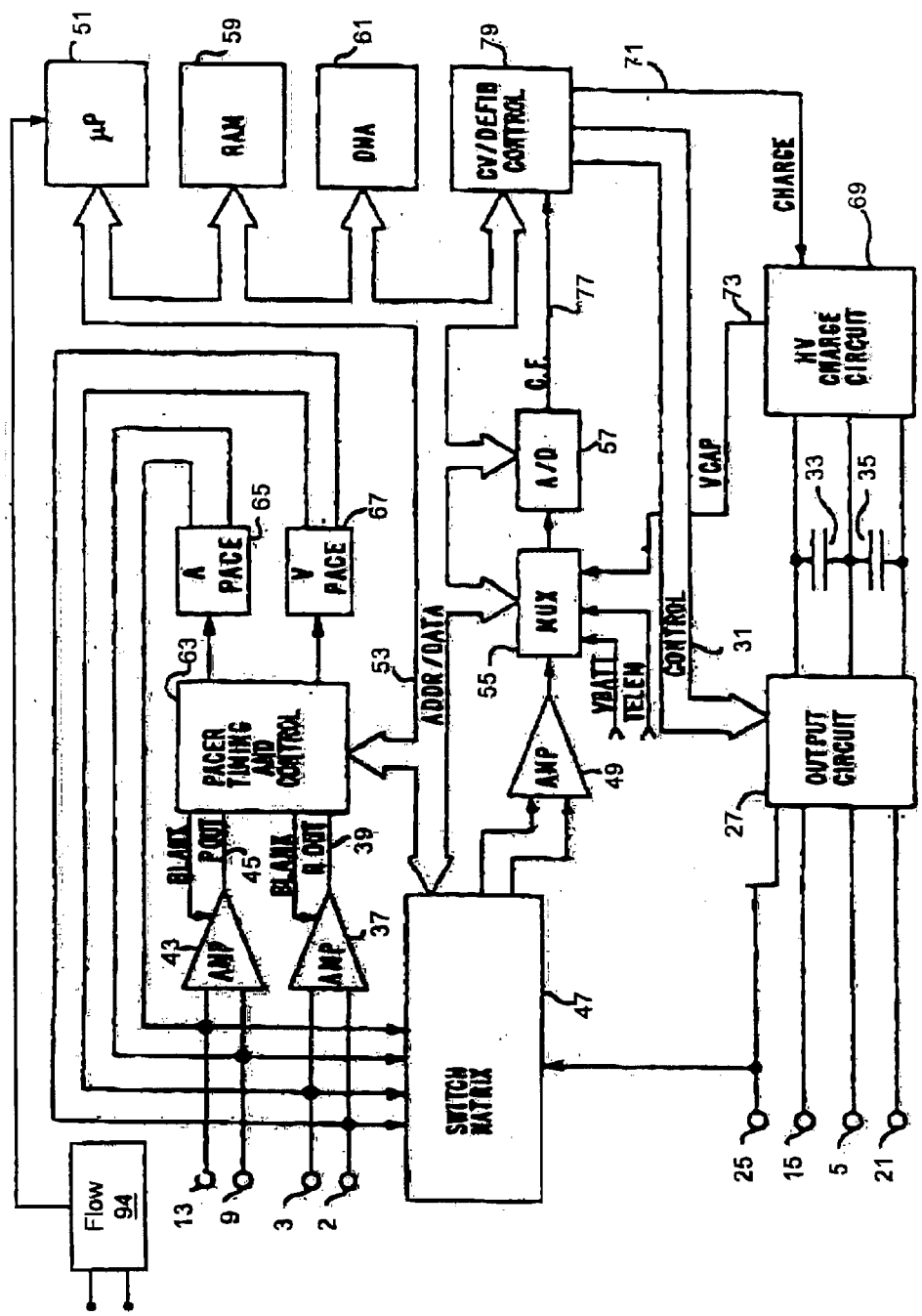
FIG. 5 is a block diagram illustrating the various components of one embodiment of an implantable pacemaker cardioverter defibrillator configured to operate in accordance with the present invention.

FIGS. 4 and 5 illustrate one embodiment in which IMD 10 is a multisite pacing system including multiple leads for providing pacing stimuli to the right atrial, the right ventricle and the surface of the left ventricle. In FIG. 4, the right ventricular lead 1 can take the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The right atrial lead 7 shown in FIG. 4 includes elongated insulative body carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within the lead body. Electrodes 13 and 9 are employed for atrial pacing and for sensing atrial depolarizations. Elongated coil electrode 19 is provided proximal to electrode 9 and coupled to the third conductor within the lead body. Electrode 19 preferably is 10 cm in length or greater and is configured to extend toward the tricuspid valve. In one embodiment of the present invention, approximately 5 cm of the right atrium electrode is located in the right atrium with the remaining 5 cm located in the SVC. At the proximal end of the lead is bifurcated connector 17 carrying three electrical connectors, each coupled to one of the coiled conductors.

The left ventricular pacing lead 41 shown in FIG. 4 is located within the coronary sinus and great vein of heart 8 and, in one configuration, can provide pacing stimuli to a surface of the left ventricle of heart 8. Left ventricular pacing lead 41 is inserted such that a blood flow sensor 22 within pacing electrode 41 produces a signal representing the flow rate of blood through the coronary sinus. In one configuration, left ventricular pacing lead 41 is a bipolar lead that includes an indifferent electrode 24 and an active electrode 26 for delivering pacing pulses. In another configuration, left ventricular pacing lead 41 is a unipolar lead having a single pacing electrode at the distal end of the lead. At the proximal end of the lead is connector plug 23 carrying an electrical connector coupled to the coiled conductor.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Flow acquisition circuit 94 acquires input signal from flow sensor 22, such as a ultrasonic Doppler transducer or of an electrochemical flow sensor, and provides digitized flow data to microprocessor 51 for further blood flow calculations.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular (AV) pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. As described in detail below, microprocessor 51 and pacing circuitry 63 control the pacing intervals as a function of the blood flow rate signal received from flow sensor 24 of left ventricular pacing lead 41. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

As explained in detail below, IMD 10 regulates the pacing pulses delivered to heart 8 as a function of the velocity of blood flowing through the coronary sinus. For example, in dual-chamber pacing systems having an atrial pacing lead 16 and a ventricular pacing 18, as illustrated in FIGS. 2 and 3, microprocessor 64 configures pacer time/control circuitry 63 to control the AV delay. The AV delay is the length of time between the delivery of an atrial pacing pulse through lead 16 and the delivery of a ventricular output pulse through lead 18. The AV delay is typically on the order to 100 milliseconds, often ranging between 120 and 150 milliseconds, and is also known as AV interval. In multisite pacing systems, as illustrated in FIGS. 4 and 5, microprocessor 51 configures the pacer time/control circuitry 63 to control the interventricular delay. The interventricular delay is the length of time between the delivery of a pacing pulse to the right ventricle through lead 1 and the delivery of a pacing pulse to the left ventricle through left ventricular pacing lead 41.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser.

No. US92/02829, Publication No. W092/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however, for example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
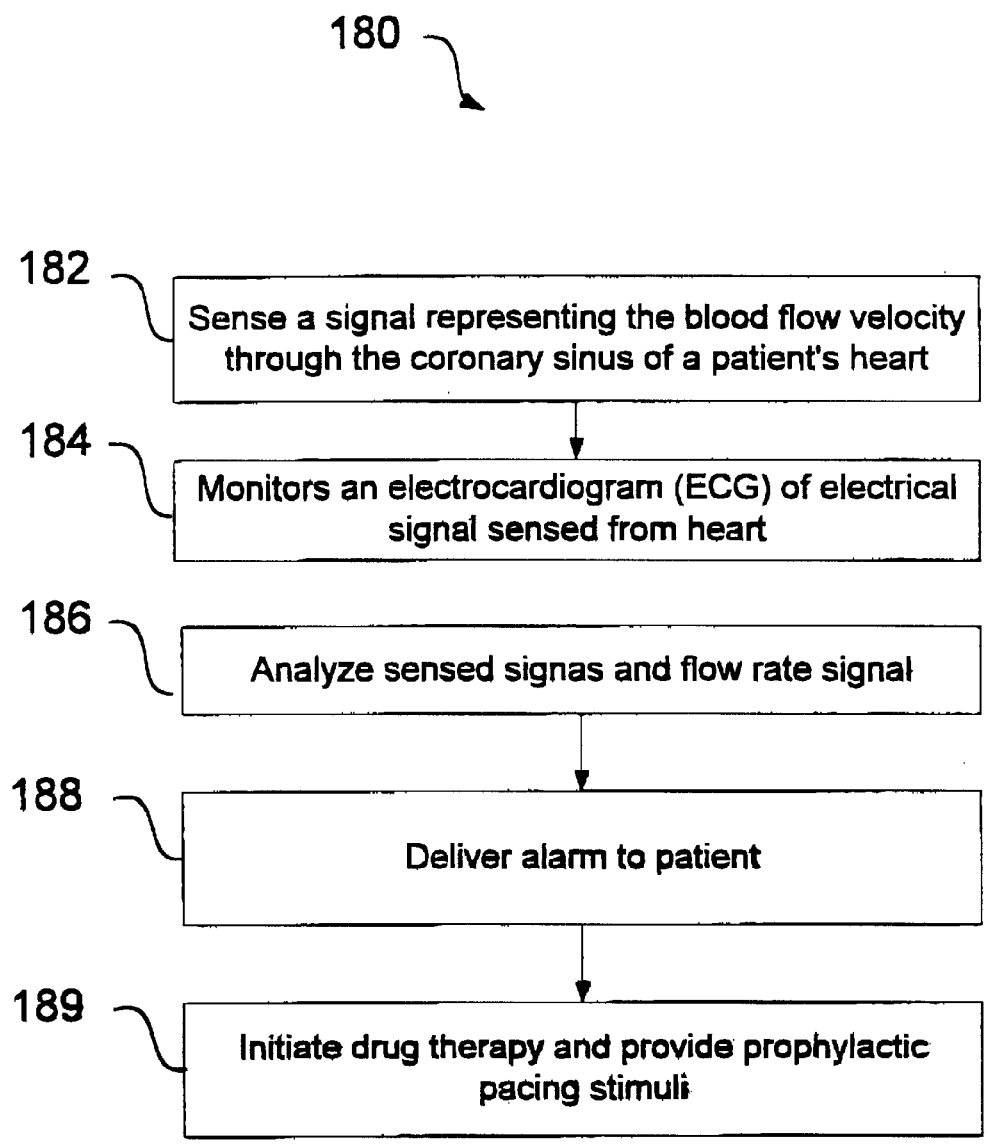
FIG. 6 is a flow chart illustrating one mode of operation of an implantable medical device operating according to the invention.

FIG. 6 is a flow chart illustrating one embodiment of a process 180 in which IMD 10 detects the potential onset of a cardiac condition, such as a myocardial infarction, by monitoring blood flow through the coronary sinus and electrical activity in the heart. Microcomputer circuit 58 senses and records a blood flow rate signal generated by flow sensor 22 of pacing lead 41 (182). The blood flow rate signal represents the velocity of the blood flowing through the coronary sinus of heart 8. Because the volume of blood flowing into the arterial system equals the volume flowing out of the venous system, the flow rate of blood exiting the coronary sinus can be used as an indicator of the coronary blood supply. In one configuration, microcomputer circuit 58 calculates an integral of the blood flow rate signal to estimate the volume of blood flowing through the coronary sinus.

In one configuration, IMD 10 additionally monitors a signal representing electrical activity sensed from heart 8 (184). For example, microcomputer circuit 58 senses and records the electrical activity during the ST segment of the heart beat, i.e., the end of ventricular depolarization (end of the R wave) and the beginning of ventricular repolarization (T wave).

Next, microcomputer circuit 58 analyzes the recorded flow rate signal and the electrical activity signal to detect a cardiac condition (186). The recorded data, representing the blood flow velocity through the coronary sinus as well as electrical activity within the heart, is useful in detecting a variety of cardiac conditions. For example, in one configuration microcomputer circuit 58 analyzes the recorded data to monitor and detect long-term ischemic heart disease. In this configuration, microcomputer circuit 58 examines the blood flow over a period of time and determines whether the blood flow through the coronary sinus has gradually degraded. Microcomputer circuit 58 can further examine the recorded electrical activity signal to detect whether a thrombus has occluded a coronary artery or whether a myocardiac infarction is pending. Microcomputer circuit 58 can detect these particular cardiac conditions by sensing a drop in blood flow through the coronary sinus followed closely by an elevation in the ST segment of the heartbeat.

In order to detect the above-described cardiac conditions, microcomputer circuit 58 employs a variety of techniques to analyze the recorded data. For example, microcomputer circuit 58 can calculate slopes for the flow rate signal and the electrical activity signal to detect sharp deviations. In addition, microcomputer circuit 58 can compare the current values of the flow rate signal and the electrical activity signal to predetermined trigger points. Microcomputer circuit 58 can also perform trend analysis on the recorded data to determine whether the flow rate signal and the electrical activity signal have gradually changed over an extended period of time.

If microcomputer circuit 58 detects the occurrence of a cardiac condition, IMD 10 delivers an alarm to the patient (188). In one configuration, IMD 10 provides an audio alarm to warn the patient that a cardiac condition has been detected such as an impending myocardial infarction. In another configuration, IMD 10 provides a muscle stimulant to the patient. In addition, microcomputer circuit 58 can initiates drug therapy by controlling a drug pump (not shown) to deliver a prescribed drug, such as a thrombolytic drug designed to dissolve any thrombus that may be occluding a coronary artery (189). Microcomputer circuit 58 may also configure the counters within digital controller/timer circuit 74 to initiate prophylactic arrhythmia pacing of heart 8.

Figure 7:
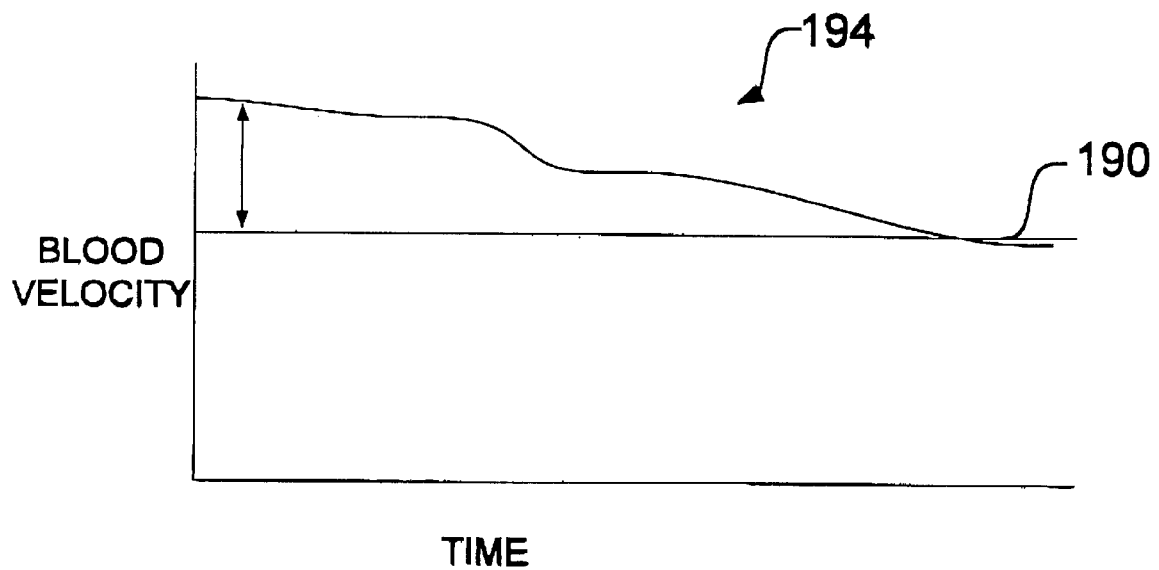
FIG. 7 illustrates mean blood flow velocity through the coronary sinus over an extended period of time.

FIG. 7 shows a trend curve 194 that graphically illustrates the mean blood flow velocity provided by flow sensor 22 as a function of time. Curve 190 illustrates a gradual drop in blood flow through coronary sinus over an extended period of time, which is indicative of long-term progression of either ischemic heart disease or a coronary sinus thrombosis. Upon crossing a trigger point 190, microcomputer circuit 58 activates an alarm indicating a detected cardiac condition. Trigger point 190 can be a programmable flow rate threshold measured in milliliters per minute, for example. Alternatively, trigger point 190 can be a programmable percentage drop, such as 25%, from a maximum of the mean flow rate of the blood through the coronary sinus as sensed by flow sensor 22.

Figure 8:
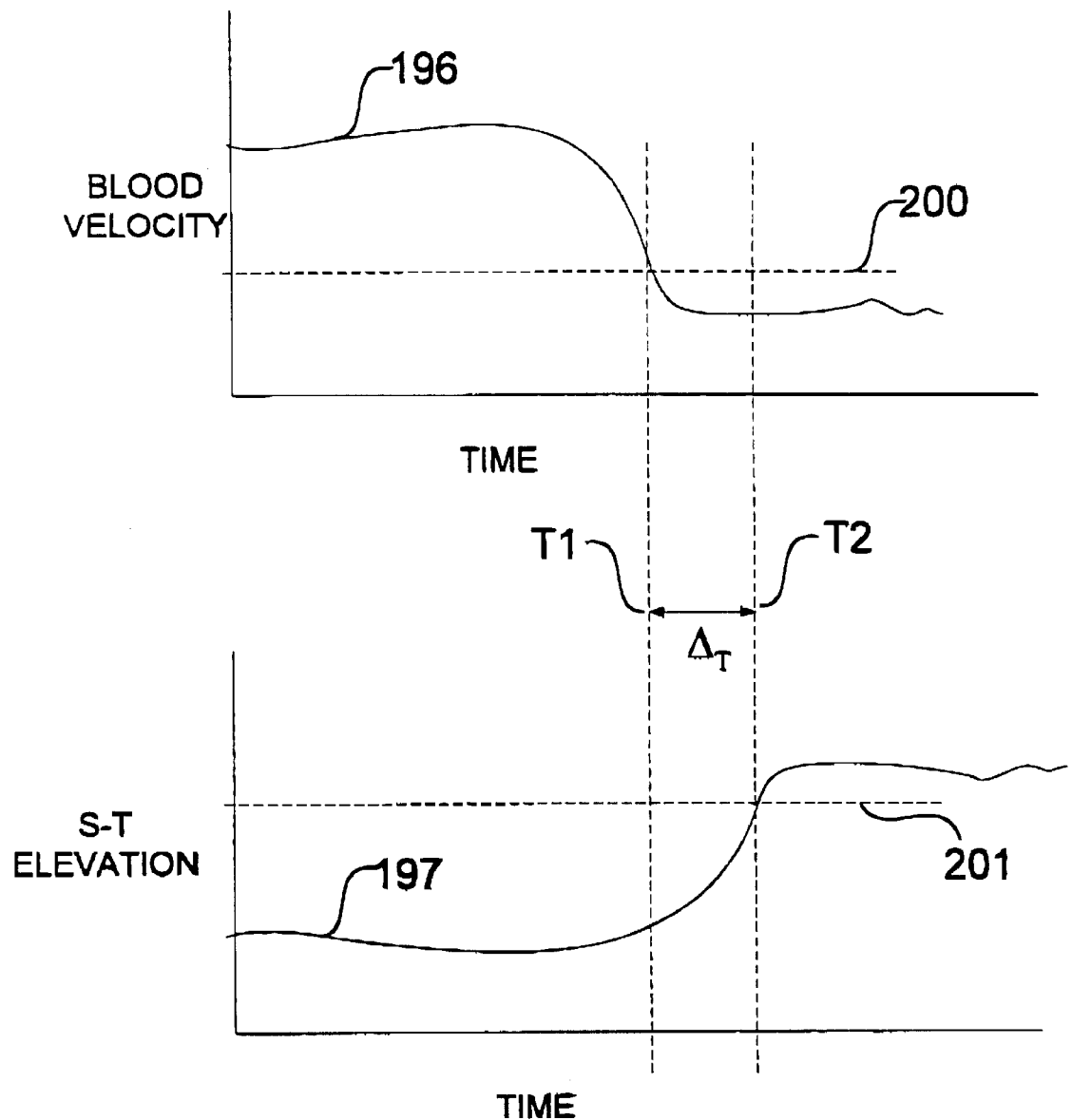
FIG. 8 illustrates mean blood flow velocity through the coronary sinus over a short period of time as well as sensed electrical activity within the heart.

FIG. 8 shows curves 196 and 197 that graphically illustrate the mean blood flow velocity signal from flow sensor 22 and the ST elevation trend sensed from heart 8, respectively. Curves 196 and 197 illustrates a sharp drop in blood flow through the coronary sinus followed closely by a sharp increase in the elevation of the ST segment of the electrocardiogram. More specifically, curve 196 drops below trigger point 200 at a time T1. Within a short period of time $\lambda_T$, such as 1 to 3 seconds, curve 197 rises over the trigger point 201 at a time T2. The sharp drop in mean blood flow through the coronary sinus followed closely by an elevation in the ST segment indicates that a thrombus has likely occluded a coronary artery and an impending myocardial infarction is likely.

The preceding specific embodiments are illustrative of the practice of the invention. It is to be understood, therefore, that other expedients known to those skilled in the art or disclosed herein, may be employed without departing from the invention or scope of the appended claims. The present invention is also not limited to detecting the presence of a thrombus or an impending myocardial infarction, but may find further application for detecting and treating other types of cardiac conditions. The present invention further includes within its scope methods of making and using the implantable medical device described above.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of wooden parts a nail and a screw are equivalent structures.

This application is intended to cover any adaptation or variation of the present invention. It is intended that this invention be limited only by the claims and equivalents thereof.

All printed publications, patent applications and patents referenced hereinabove are incorporated by reference herein, each in its respective entirety.

What is claimed is:

1. An implantable medical device system comprising:
    a sensor to output a blood flow rate signal representing a rate of blood flow through a coronary sinus of a patient's heart;
    an implantable medical device (IMD) coupled to the sensor;
    a circuit embedded within the IMD configured to analyze the blood flow rate signal and an ST signal; and,
    an implantable lead to coupled to the circuit embedded within the IMD, the implantable lead configured to output the ST signal sensed from the patient's heart;
    wherein a cardiac condition is detected when the circuit embedded in the IMD detects a sharp drop in the blood flow rate followed in more than one second by a sharp elevation in the ST signal.

2. The system of claim 1, wherein the cardiac condition includes ischemic heart disease.

3. The system of claim 1, wherein the cardiac condition includes a myocardial infarction.

4. The system of claim 1, wherein the cardiac condition includes a thrombus occluding a coronary artery.

5. The system of claim 1, wherein a microcomputer circuit is configured to determine a rate of change for the blood flow rate signal.

6. The system of claim 1 further comprising a drug deliver system to provide a therapeutic drug when the IMD detects the cardiac condition.

7. The system of claim 6, wherein the therapeutic drug is a thrombolytic.

8. The system of claim 1, wherein the sensor is integrated in a coronary sinus lead for implantation in the coronary sinus of the patient's heart.

9. The system of claim 1, wherein the IMD includes an alarm activated by a microcomputer circuit when the cardiac condition is detected.

10. The system of claim 9, wherein the alarm comprises an audible alarm.

11. The system of claim 9, wherein the alarm comprises a muscle-stimulating device.

12. The system of claim 1 further comprising a pacing lead coupled to the IMD, and further wherein the IMD comprises pacing control circuit to deliver pacing pulses as a function of the sensed blood flow rate signal and a sensed electrical activity.

13. The system of claim 1, wherein a microcomputer circuit is configured to log the sensed blood flow rate signal over a period of time, and further wherein the microcomputer circuit detects the cardiac condition by analyzing a trend of the blood flow rate signal.

14. The system of claim 1 and further including a defibrillation electrode to carry defibrillation pulses from the IMD to the patient's heart.

15. The system of claim 1, wherein a microcomputer circuit is configured to calculate the integral of the blood flow signal.

16. A method for pacing a patient's heart using an implanted medical device comprising:

sensing a rate of blood flow through a coronary sinus of a patient's heart;

sensing an ST signal from a patient's heart;

detecting a cardiac condition when there is a sharp drop in the rate of blood flow followed in more than one second by a sharp elevation in the ST signal.

17. The method of claim 16, wherein detecting the cardiac condition includes detecting ischemic heart disease.

18. The method of claim 16, wherein detecting the cardiac condition includes detecting a myocardial infarction.

19. The method of claim 16, wherein detecting the cardiac condition includes detecting a thrombus occluding a coronary artery.

20. The method of claim 16 further including calculating a rate of change for the blood flow.

21. The method of claim 16 further comprising delivering a therapeutic drug when the cardiac condition is detected.

22. The method of claim 16, wherein the therapeutic drug is a thrombolytic.

23. The method of claim 16 further including activating an alarm when the cardiac condition is detected.

24. The method of claim 23, wherein activating an alarm includes activating an audible alarm.

25. The method of claim 23, wherein activating an alarm includes activating a musclestimulating alarm.

26. The method of claim 16 further including deliver pacing pulses as a function of the sensed blood flow rate signal and the sensed electrical activity.

27. The method of claim 16 further including:

logging the sensed blood flow rate signal over a period of time; and analyzing the log to detect the cardiac condition.

28. The method of claim 16 further including calculating the integral of the sensed blood flow.

* * * * *